(12) United States Patent
Coral

(10) Patent No.: US 9,775,871 B2
(45) Date of Patent: Oct. 3, 2017

(54) HERBAL COMPOSITIONS AND METHODS FOR TREATING HEPATIC DISORDERS

(75) Inventor: Jose Gonzalo Cabanillas Coral, Iquitos (PE)

(73) Assignees: SABELL CORPORATION, Calgary (CA); Jose Gonzalo Cabanillas Coral, Iquitos (PE)

( * ) Notice: Subject to any disclaimer, the term of this patent is extended or adjusted under 35 U.S.C. 154(b) by 1266 days.

(21) Appl. No.: 12/681,066

(22) PCT Filed: Oct. 3, 2008

(86) PCT No.: PCT/CA2008/001764
§ 371 (c)(1),
(2), (4) Date: Jun. 22, 2010

(87) PCT Pub. No.: WO2009/043167
PCT Pub. Date: Apr. 9, 2009

(65) Prior Publication Data
US 2010/0260874 A1 Oct. 14, 2010

Related U.S. Application Data

(60) Provisional application No. 60/977,256, filed on Oct. 3, 2007.

(51) Int. Cl.
*A61K 36/57* (2006.01)
*A61K 36/30* (2006.01)
*A61K 36/9066* (2006.01)

(52) U.S. Cl.
CPC .............. *A61K 36/30* (2013.01); *A61K 36/57* (2013.01); *A61K 36/9066* (2013.01)

(58) Field of Classification Search
None
See application file for complete search history.

(56) References Cited

U.S. PATENT DOCUMENTS

| | | | |
|---|---|---|---|
| 5,401,777 A | 3/1995 | Ammon et al. | |
| 5,861,415 A | 1/1999 | Majeed et al. | |
| 6,426,098 B1 | 7/2002 | Yang Jr. | |
| 6,841,177 B1 | 1/2005 | Almagro et al. | |
| 2005/0048008 A1* | 3/2005 | Gupta | 424/59 |
| 2005/0084547 A1* | 4/2005 | Subbiah | 424/740 |

FOREIGN PATENT DOCUMENTS

| | | |
|---|---|---|
| CN | 1593495 | 3/2005 |
| EP | 1032408 | 7/2002 |
| JP | 5262659 | 10/1993 |
| WO | WO 03/051380 | 6/2003 |
| WO | WO 2004/048358 | 6/2004 |

OTHER PUBLICATIONS

Bussman et al., Blending Traditional and Western Medicine: Medicinal plant use among patients at Clinica Anticona in El Porvenir, Peru, Jun. 2007, Ethnobotany Research & Applications, 5: 185-199.*
Bussman et al., Jun. 2007, Ethnobotany Research & Applications, 5: 185-199 and supplement.*
Afzal, M., et al. Antioxidant Activity of Cordia Myxxa L. and its Hepatoprotective Potential. 2007. Electronic Journal of Environmental, Agricultural and Food Chemistry. vol. 6(6), pp. 2109-2118.
Al-Awadi, F.M., et al. Antiinflammatory Effects of Cordia myxa Fruit on Experimentally Induced Colitis in Rats. 2001. Nutrition vol. 17, pp. 391-396.
Baskar, R., et al. In vitro Antioxidant Studies in Leaves of Annona Species. 2007. Indian J Exp Biol. vol. 45(5), pp. 480-485.
Bayeux, M., et al. Evaluation of the Antiedematogenic Activity of Artemetin Isolated From Cordia curassavica DC. 2002. Brazilian Journal of Medical and Biological Research. vol. 35, pp. 1229-1232.
Berry, M.N. and Friend, D.S. High Yield Preparation of Isolated Rat Liver Parenchymal Cells. 1969. J Cell Biol. vol. 43, pp. 506-520.
Boots, A.W., et al. No Role of DT-Diaphorase (NqO1) in the Protection Against Oxidized Quercetin. 2005. FEBS Lett. vol. 579, pp. 677-682.
Bussmann R.W., et al. Traditional Medicinal Plant Use in Northern Peru: Tracking Two Thousand Years of Healing Culture. 2006. J Ethnobiol Ethnomed. vol. 2, p. 47. www.ethnobiomed.com/content/2/1/47.
Chhabra, S.C., et al. Phytochemical Screening of Tanzanian Medical Plants. 1984. J Ethnopharmacol. vol. 11(2), pp. 157-179.
Davis, G.L. Combination Therapy with Interferon Alpha and Ribavirin as Treatment of Interferon Relapse in Chronic Hepatitis C. 1999. Semin Liver Dis. vol. 19(Suppl 1), pp. 49-55.
De Souza, G., et al. Ethnopharmacological Studies of Antimicrobial Remedies in the South of Brazil. 2004. Journal of Ethnopharmacology. vol. 90, pp. 135-143.
Deshpande, U.R., et al. Protective Effect of Tumeric (*Curcuma longa* L.) Extract on Carbon Tetrachloride-Induced Liver Damage in Rats. 1998. Indian J Exp Biol. vol. 36(6), pp. 573-577.
Ficarra, R., et al. Leaf Extracts of Some Cordia Species: Analgesic and Anti-Inflammatory Activities as Well as Their Chromatographic Analysis. 1995. II Farmaco. vol. 50(4), pp. 245-256.
Hernandez, T., et al. Ethnobotany and Antibacterial Activity of Some Plants Used in Traditional Medicine of Zapotitlan de las Salinas, Puebla (Mexico). 2003. Journal of Ethnopharmacology. vol. 88, pp. 181-188.
Hernandez, T., et al. Antimicrobial Activity of the Essential Oil and Extracts of Cordia curassavica (Boraginaceae). 2007. Jounal of Ethnopharmacology. vol. 111, pp. 137-141.
Hirose, M., et al. Modifying Effects of the Naturally Occurring Antioxidants Gamma-oryzanol, Phytic Acid, Tannic Acid and n-Tritriacontane-16,18-dione in a Rat Wide-Spectrum Organ Carcinogenesis Model. 1991. Carcinogenesis. vol. 12, pp. 1917-1921.
James, L.P., et al. Acetaminophen-Induced Hepatotoxicity. 2003. Drug Metabolism Disposition. vol. 31, pp. 499-506.
Kloucek, P. Antimicrobial Activity of Some Medicinal Barks Used in Peruvian Amazon. 2007. Journal of Ethnopharmacology. vol. 111, pp. 427-429.

(Continued)

*Primary Examiner* — Terry A McKelvey
*Assistant Examiner* — Catheryne Chen

(57) ABSTRACT

Herbal compositions and their use in the prevention and/or treatment of hepatitis are provided The herbal compositions comprise an extract of flowers, leaves, and roots from the plant genera *Cordia*, *Annona*, and *Curcuma*, respectively, wherein the specific species are *Cordia lutea*, *Annona muricata* and *Curcuma longa*.

11 Claims, No Drawings

(56) References Cited

OTHER PUBLICATIONS

Kunchandy, E., and Rao, M.N.A. Effect of curcumin on hydroxyl radical generation through Fenton reaction. 1989. Int J Pharm. vol. 57, pp. 173-176.
Lans, C. Ethnomedicines Used in Trinidad and Tobago for Reproductive Problems. 2007. Journal of Ethnobiology and Ethnomedicine. vol. 3(13), pp. 1-12.
Lautraite, S., et al. Optimisation of Cell-Based Assays for Medium Throughput Screening of Oxidative Stress. 2003. Toxicol in vitro. vol. 17, pp. 207-220.
Lin, Y.L., et al. Anti-lipid-peroxidative Principles from Tounefortia samentosa. 2002. J Nat Prod. vol. 65(5), pp. 745-747.
Liu, J., et al. The Effects of 10 Triterpenoid Compounds on Experimental Liver Injury in Mice. 1994. Fundamental and Applied Toxicology. vol. 22, pp. 34-40.
Luper, S. A Review of Plants Used in the Treatment of Liver Disease: Part Two. 1999. Alternative Medicine Review. vol. 4(3), pp. 178-188.
McHutchison, J.G., and Poynard, T. Combination Therapy with Interferon Plus Ribavirin for the Initial Treatment of Chronic Hepatitis C. 1999. Semin Liver Dis. vol. 19(Suppl 1), pp. 57-65.
Medeiros, R., et al. Effect of Two Active Compounds Obtained from the Essential Oil of Cordia verbenacea on the Acute Inflammatory Responses Elicited by LPS in the Rat Paw. 2007. British Journal of Pharmacology. pp. 1-10.
Middleton Jr., E., et al. The Effects of Plant Flavonoids on Mammalian Cells: Implications for Inflammation, Heart Disease, and Cancer. 2000. Pharmacol Rev. vol. 52, pp. 673-751.
Miyamoto, K.I., et al. Antitumor Activities of Ellagitannins Against Sarcoma-180 in Mice. 1993. Biol Pharm Bull. vol. 16, pp. 379-387.
Molina-Salinas, G., et al. Evaluation of the Flora of Northern Mexico for in vitro Antimicrobial and Antituberculosis Activity. 2007. Journal of Ethnopharmacology. vol. 109, pp. 435-441.
Mora S., et al. Anxiolytic and Antidepressant-like Effects of the Hydroalcohol Extract from Aloysia polystachya in Rats. 2005. Pharmacol Biochem Behav. vol. 82(2), pp. 373-378.
Okuda, T., et al. Studies on the Activities of Tannins and Related Compounds from Medicinal Plants and Drugs. I. Inhibitory Effects on Lipid Peroxidation in Mitochondria and Microsomes of Liver. 1983. Chem Pharm Bull. vol. 31, pp. 1625-1631.
Passos, G., et al. Anti-Inflammatory and Anti-Allergic Properties of the Essential Oil and Active Compounds from Cordia verbenacea. 2007. Journal of Ethnopharmacology. vol. 110, pp. 323-333.
Raintree Nutrition Monograph. 2004. pp. 1-10. www.rain-tree.com/Graviola-Monograph.pdf.
Raj, H.G., et al. Mechanism of Biochemical Action of Substituted 4-Methylbenzopyran-2-ones. Part I: Dioxygenated 4-methyl Coumarins as Superb Antioxidant and Radical Scavenging Agents. 1998. J Bioorg Med Chem. vol. 6, p. 833.
Reddy, A.C., and Lokesh, B.R. Effect of Dietary Tumeric (*Curcuma longa*) on Iron-induced Lipid Peroxidation in the Rat Liver. 1994. Food Chem Toxicol. vol. 32, pp. 279-283.
Refouvelet, B., et al. Synthesis of 4-Hydroxycoumarin and 2,4-quinolinediol Derivatives and Evaluation of Their Effects on the Viability of HepG2 Cells and Human Hepatocytes Culture. 2004. European Journal of Medicinal Chemistry. vol. 39, pp. 931-937.
Rui, Y.C. Advances in Pharmacological Studies of Silymarin. 1991. Mem Inst Oswaldo Cruz. vol. 86, pp. 79-85.
Satoh, K., and Sakagami, H. Ascorbyl Radical Scavenging Activity of Polyphenols. 1996. Anticancer Res. vol. 16, pp. 2885-2890.
Scevola, D., et al. Flavonoids and Hepatic Cyclic Monophosphates in Liver Injury. 1984. Boll Ins Sieroter Milan. vol. 63, pp. 77-82.
Sertie, J., et al. Pharmacological Assay of Cordia verbenacea III: Oral and Topical Antiinflammatory Activity and Gastrotoxicity of a Crude Leaf Extract. 1991. Journal of Ethnopharmacology. vol. 31, pp. 239-247.
Siddiqui, B., et al. Studies on the Chemical Constituents of the fruits of Cordia latifolia. 2006. Natural Product Research. vol. 20(2), pp. 131-137.
Sreejayan, N., and Rao, M.N. A. Nitric Oxide Scavenging by Curcuminoids. 1997. J Pharm Pharmacol. vol. 49, pp. 105-107.
Sunitha, S., et al. Hepatoprotective Effect of Lupeol and Lupeol Linoleate on Tissue Antioxidant Defence System in Cadmium-induced Hepatotoxicity in Rats. 2001. Fitoterapia. vol. 72, pp. 516-523.
Takeda, S. and Aburada, M.J. The Choleretic Mechanism of Coumarin Compounds and Phenolic Compounds. 1981. Pharmacobiodyn. vol. 4, p. 724-734.
Ticli, F., et al. Rosmarinic Acid, A New Snake Venom Phospholipase A2 Inhibitor from Cordia verbenacea (Boraginacea): Antiserum Action Potentiation and Molecular Interaction. 2005. Toxicon. vol. 46, pp. 318-327.
Zhu, M., et al. Triterpene Antioxidants from Ganoderma lucidum. 1999. Phytotherapy Research. vol. 13, pp. 529-531.
Joyeux, M et al., Screening of Antiradical, Antilipoperoxidant and Hepatoprotective Effects of nine Plant Extracts Used in Caribbean Fold Medicine, Phytotherapy Research, 1995, p. 228-230, vol. 9(3).
Chang, F-R et al., New Adjacent Bis-Tetrahydrofuran Annonaceous Acetogenins from Annona Muricata, Planta Medica, 2003, p. 241-246, vol. 69(3).
Guiterrez, A et al., Medicinal Plants of the Tunal, District of Lalaquiz, Huancabamba, Piura, Peru, Acta Pharmacologica Sinica, 2006, p. 332, vol. 26(Suppl).
Xing L. Compound Medicine for Treating Cancer, in Which the Medicament is Prepared from Total Annona Squamosa Polygoni Multiflori Curcuma Aromatica, WPI, 2005, vol. 2005(77).
Opposition Papers received from Indian Patent Office in respect of Indian patent application 889/MUMNP/2010, Jan. 29, 2015.
Bussmann R.W., et al. Traditional Medicinal Plant Use in Northern Peru: Tracking Two Thousand Years of Healing culture. 2006. J Ethnobiol Ethnomed. 2:47, pp. 1-18. www.ethnobiomed.com/content/2/1/47. See Additional file 1. Species encountered and used in Northern Peru. pp. 1-82. www.ethnobiomed.com/content/supplementary/1746-4269-2-47-s1.pdf.
Bussmann R.W., et al. Blending Traditional and Western Medicine: Medicinal plant use among patients at Clinica Anticona in El Porvenir, Peru. 2007. Ethnobotany Research & Applications. vol. 5, pp. 185-199. http://hdl.handle.net/10125/230.

* cited by examiner

HERBAL COMPOSITIONS AND METHODS FOR TREATING HEPATIC DISORDERS

CROSS REFERENCE TO RELATED APPLICATIONS

This is a 35 USC 371 national stage of international application PCT/CA2008/001764 filed Oct. 3, 2008 which claims priority to U.S. Provisional Patent Application No. 60/977,256 filed Oct. 3, 2007.

FIELD OF THE INVENTION

The present application relates to novel herbal compositions and their use in the prevention and/or treatment of hepatic disorders. More particularly, the herbal compositions of the present application comprise at least one species of the plant genera *Cordia, Annona* or *Curcuma*, or extracts thereof, or combinations thereof.

BACKGROUND OF THE INVENTION

The formation of oxygen radical species (ORS) is involved in the pathogenesis of many acute and chronic diseases, ranging from inflammatory-immunologic diseases to myocardial infarction and cancer. Some of the deleterious effects from the excessive formation of ORS include lipid peroxidation of the membrane lipids, oxidative damage to nucleic acids and carbohydrates, as well as oxidation of sulfhydryl proteins and other sensitive groups. The defence provided by antioxidant systems is essential for survival. Detoxification of the ORS in a cell is carried on by enzymatic and non-enzymatic systems which constitute the antioxidant defence system (Middleton Jr. E., Chithan K., and Heoharides T. C. The Effects of Plant Flavonoids on Mammalian Cells: Implications for Inflammation, Heart Disease, and Cancer. *Pharmacol Rev* 52:673-751, 2000).

Lipid peroxidation can be biologically important in the exacerbation of a tissue lesion due to the potential cytotoxicity of the final products resulting from peroxidation. For example, products of lipid peroxidation of the cells may be carcinogenic. Recently, emphasis has been put on the role that lipid peroxidation plays in the development of arteriosclerosis, strokes, myocardial infarction, damage to the brain and spinal cord after suffering ischemia, cancer, inflammation, iron toxicity, and hepatotoxicity induced by chemical and biological agents (Middleton Jr. E., Chithan K., and Heoharides T. C. The Effects of Plant Flavonoids on Mammalian Cells: implications for Inflammation, Heart Disease, and Cancer. *Pharmacol Rev* 52:673-751, 2000).

Chronic hepatic diseases cause thousands of deaths in the world every year and are the tenth leading cause of death in the United States. Currently, hepatic disorders, particularly those caused by viral infections, are a serious health issue, and their successful treatment constitutes a big challenge. There is no effective treatment for a majority of the hepatopathies. Currently some patients with viral hepatitis are treated with Interferon (IFN); however, IFN therapy has been successful only in about 25% of the cases.

IFN is not available to all the patients, as the six-month therapy required is expensive. In addition, this treatment has several secondary effects like severe flu-like symptoms, lethargy, hair loss, and bad taste in the mouth. IFN attacks the virus via the immune system, but it does not reverse the damage caused by the infection, like hepatic cirrhosis or diminished functionality of the spleen.

Other treatments, such as Ribavirin therapy, improve the results in medical and histological exams, especially in combination with IFN. However, costs of treatment are also high and there is a significant risk of suspending the treatment due to adverse effects (Mc Hutchison, J. G. and Poynard T. Combination therapy with interferon plus Ribavirin for the initial treatment of chronic Hepatitis C. *Semin Liver Dis* 1999; 19 (suppl 1): 57-65; Davil G. L. Combination therapy with interferon alpha and Ribavirin as treatment of interferon relapse in chronic hepatitis C. *Semin Liver Dis* 1999; 19 (suppl 1): 49-55).

The World Health Organisation (WHO) estimates that 3% of the world's population has been infected with Hepatitis C, and that there are around 170 million chronic carriers who are at risk for developing cirrhosis and/or liver cancer. The WHO cannot afford to treat 170 million people in the world with medications like Rebetron, which consists of Ribavirin and Interferon alpha 2B, whose treatment costs USD 2,000 per month, for 6-12 months; in addition, these treatments require extensive medical support to manage the adverse effects caused by the medications.

Since there is no therapy or synthetic medication effective and safe enough to treat hepatopathies, many patients have turned to alternative medicine based on natural elements. Despite significant progress in modern medicine, medicinal plants remain as a necessary element when it comes to developing accurate, safe and effective treatments for hepatic disorders. In recent years, there has been a shift towards the therapeutic evaluation of herbal products to treat liver diseases, some of which are proving safe and moderately effective.

Several scientific publications point out the fact that many groups of metabolites from vegetal origin show antioxidant and hepatoprotective activity. This is observed particularly amongst phenols, especially those belonging to the benzenoid group, where tournefolal, tournefolic acids A and B, and the ethylester from the tournefolic acid, isolated from the aerial parts, that is, the stem, leaves, flowers and fruit, of the *Tournefortia sarmentosa*, show antioxidant activity and inhibit the peroxidation of low-density lipoproteins (Lin Y. L., Chang Y. Y., Kuo Y. H., Shiao M. S. Anti-lipid-peroxidative principles from *Tounefortia samentosa*. *J Nat. Prod.* 2002 May; 65(5):745-7). Curcumin, also a benzenoid, shows a captivating activity on superoxide anions (Kunchandy E., Rao M. N. A. *Int. J. Pharmaceut.*, 57: 173-176 (1989)) and nitric acid (Sreejayan N., Rao M. N. A. *J. Pharm. Pharmacol.*, 49: 105-107 (1997)) in experimental models showing the inhibition of lipid peroxidation in rat liver (Reddy A. C., Lokesh B. R. *Food Chem. Toxicol.*, 32: 279-283 (1994)).

Other phenolic elements, such as tannins, show antioxidant (Satoh, K., Sakagami, H., 1996. Ascorbyl radical scavenging activity of polyphenols. *Anticancer Res.* 16: 2885-2890) and hepatoprotective (Miyamoto, K. I., Nomura, M., Murayama, T., Furukawa, T., Hatano, T., Yashida, T., Koshiura, R., Okuda, T., 1993. Antitumor activities of ellagitannins against sarcoma-180 in mice. *Biol. Pharm. Bull.* 16: 379-387) activity, inhibiting lipid peroxidation in hepatic microsomes and mitochondria (Okuda T., Kimuar Y., Yoshida T., Hatano T., Okunda H., Arichi S. Studies on the activities of tannins and related compounds from medicinal plants and drugs. I. Inhibitory effects on lipid peroxidation in mitochondria and microsomes of liver. *Chem. Pharm. Bull.* 31: 1625-1631 (1983)). Tannic acid reduced the incidence of hepatic neoplasia in mice (Hirose M., Ozaki K., Takaba K., Fukushima S., Shirai T., Ito, N. Modifying effects of the naturally occurring antioxidants gamma— oryzanol, phytic acid, tannic acid and n-tritriacontane-16, 18-dione in a rat wide-spectrum organ carcinogenesis model. *Carcinogenesis* 12: 1971-1921 (1991)). Results from extensive clinical research showed the effectiveness and safety of the polyphenols when it comes to treating hepatobiliary dysfunctions and digestive problems, such as a sensation of fullness, loss of appetite, nausea and abdominal pain. In addition, these elements have been found to have preventive and hepatoprotective effects against gastropathy induced by non-steroidal anti-inflammatories (Ruiyc. Advances in pharmacological studies of silymarin. *Mem Inst Oswaldo Cruz* 1991; 86:79-85; Scevola D, Barbacini G, Grosso A, Bona S, Perissoud D. Flavonoids and hepatic cyclic monophosphates in liver injury. *Boll Ins Sieroter Milan* 1984; 63:77-82).

Coumarins are another kind of polyphenolic compounds that can be found in abundance in the vegetable kingdom. Many of them show interesting biological activity, for instance, the 4-methoxycoumarins have cholerectic properties (Takeda, S.; Aburada, M. *J. Pharmacobio-Dyn.* 4: 724 (1981)). The 7,8 dihydroxy-4-methylcoumarin and the 7,8-diacetoxy-4-methylcoumarin have antioxidant properties, and thus are considered effective scavengers of oxygen radicals (Raj, H. G.; Parmar, V. S.; Jain, S. C.; Priyadarsini, K. I.; Mittal, J. P.; Goel, S.; Poonam; Himanshu; Malhotra, S.; Singh, A.; Olsen, C. E.; Wngel, *J. Bioorg. Med. Chem.* 6: 833 (1998)). In addition, this group of molecules show protective effects against toxicity induced by a known oxidant (t-butylhydroperoxide) in HepG2 cells and primary human hepatocyte cultures (Bernard Refouvelet, Catherine Guyon, Yves Jacquot, Corinne Girard, Herve Fein, Francoise Bevalotb, Jean-Francois Robert a, Bruno Heyd, Georges Mantion, Lysiane Richert, Alain Xicluna, Synthesis of 4-hydroxycoumarin and 2,4-quinolinediol derivatives and evaluation of their effects on the viability of HepG2 cells and human hepatocytes culture. *European Journal of Medicinal Chemistry* 39: 931-937 (2004)).

The terpenoids are other group of metabolites derived from plants that also show antioxidant (Zhu M, Chang Q, Wong L K, Chong F S, Li R C. Triterpene antioxidants from *Ganoderma lucidum*. *Phytotherapy Research* 13: 529-31 (1999)) and hepatoprotective (James, L. P., Mayeux, P. R., Honson, J. A. Acetaminophen-induced hepatotoxicity. *Drug Metabolism Disposition* 31: 499-506 (2003)) activity. Triterpene celastrol shows a powerful inhibitory effect against lipid peroxidation in the hepatic mitochondria. In vitro and in vivo experiments, as well as other clinical tests, have shown the effects of gastroprotective (Zhu M, Chang Q, Wong L K, Chong F S, Li R C. Triterpene antioxidants from *Ganoderma lucidum*. *Phytotherapy Research* 13: 529-31 (1999)) and hepatoprotective activity of several terpenoids, such as the oleanic acid, ursolic acid, alpha-hederine, glycyrrhizin and lupeol (Liu, J., Liu, Y., Mao, Q. The effects of 10 triterpenoid compounds on experimental liver injury in mice. *Fundamental and Applied Toxicology* 22: 34-40 (1994)) (Sunitha S., Nagaraj M., Varalakshmi P. Hepatoprotective effect of lupeol and lupeol linoleate on tissue antioxidant defence system in cadmium-induced hepatotoxicity in rats. *Fitoterapia* 72: 516-523 (2001)).

There is a need for a safe and effective treatment for viral and non-viral hepatic disorders that address some of the disadvantages of current treatment methods.

SUMMARY OF THE INVENTION

According to a broad aspect of the invention, herbal compositions are provided comprising at least one species of the plant genera *Cordia*, *Annona* or *Curcuma*, or combinations thereof. In one embodiment, the at least one species is a species of the plant genus *Cordia*, for example, *Cordia lutea*. In another embodiment, the herbal composition comprises a species of each of the plant genera *Cordia*, *Annona* and *Curcuma*.

In another embodiment, an herbal composition is provided comprising *Cordia* spp flowers, *Annona* spp leaves, or *Curcuma* spp roots, or combinations thereof. In a further embodiment, an herbal composition is provided comprising *Cordia lutea* flowers, *Annona muricata* leaves and *Curcuma longa* roots. The herbal compositions of the present invention are useful for the prevention and/or treatment of hepatic disorders.

In another broad aspect, the invention is related to herbal compositions comprising extracts of at least one of the plant genera *Cordia*, *Annona* and *Curcuma*, or combinations thereof. In one embodiment, an herbal composition is provided comprising an extract from a species of the plant genus *Cordia*, for example, *Cordia lutea*. In one embodiment, the herbal composition comprises an extract of *Cordia* in combination with either *Annona* or *Curcuma* or both. In another embodiment, the herbal composition comprises an extract from a species of each of the plant genera *Cordia*, *Annona* and *Curcuma*.

In another embodiment, an herbal composition is provided comprising an extract of *Cordia* spp flowers, *Annona* spp leaves, or *Curcuma* spp roots, or combinations thereof, for use in the prevention and treatment of hepatic disorders. In a further embodiment, the herbal composition comprises extracts, for example, hydroalcoholic extracts, of at least one of *Cordia lutea* flowers, Annona muricata leaves, or *Curcuma longa* roots, or combinations thereof. It is understood that other solvents than hydroalcohol can also be used such as water, hexanes, chloroform and the like. In a further embodiment, the herbal composition comprises hydroalcoholic extracts of *Cordia lutea* flowers, *Annona muricata* leaves and *Curcuma longa* roots.

Each of *Cordia spp*, *Annona* spp and *Curcuma* spp, or extracts thereof, exhibit significant hepatoprotective properties and are effective in the prevention and/or treatment of hepatic disorders. *Cordia* spp, and extracts thereof, was particularly effective. Surprisingly, however, it was discovered that the various combinations of *Cordia* spp, *Annona* spp and *Curcuma* spp, or extracts thereof, and, in particular, the combination of *Cordia* spp, *Annona* spp and *Curcuma* spp, or extracts thereof, showed an additional synergism, suggesting that the effectiveness and/or properties of each of the plants act together. Particularly effective were combinations of *Cordia* spp, *Annona* spp and *Curcuma* spp, or extracts thereof, in a weight ratio of 1:1:1, more preferably, 5:1:1, and even more preferably, 8:1:1, respectively. In another embodiment, the weight ratio of *Cordia* spp:*Annona* spp:*Curcuma* spp, or extracts thereof, is 1:0.05-1:0.05-1. In one aspect, the concentration of *Curcuma* spp in mixtures should not exceed the concentration of *Cordia* spp or *Annona* spp.

At least one of the advantages of the herbal compositions of the present invention is their safety and effectiveness. For example, the herbal compositions comprising extracts of the plant genera of interest were found to be non-toxic at cell and tissue level, non-toxic in acute toxicity studies in mice and rats, and to be safe for human use.

The herbal compositions of the present invention could also act prophylactically through prevention of viral infection or other agents that cause hepatic disorders. Therefore, they can be used to treat hepatic disorders caused by viral infection, autoimmune reactions, consumption of xenobiotics and all those disorders that could compromise hepatic function. Treatment can be therapeutic and/or prophylactic.

The herbal compositions of the present invention can be administered orally or parenterally (topical, rectal, intravenous, intramuscular or hypodermic). Treatment can be administered orally in a liquid or solid form (e.g., tablet), in one dose, multiple doses or through a slow-discharge or deposit method. In the alternative, herbal compositions can be in the form of a tea-like substance where hot water can be added to form a hot or cold drink.

In another broad aspect of the present invention, a method is provided to obtain hydroalcoholic extracts from a selected plant organ for use in the preparation of an herbal composition of the present invention, comprising:

drying the selected plant organ and grinding the dried plant organ to obtain a powder having a particle size in range of about 0.35 mm to about 0.1 mm;

macerating the powder in a hydroalcoholic solution for about 6 to about 8 days at around room temperature to obtain an extract of the plant organ;

concentrating the extract by evaporation in a rotoevaporator; and freeze drying and sterilising the extract.

It is understood that other concentrating methods known in the art can also be used.

The herbal compositions of the present invention possess antioxidant activity in isolated hepatocytes in rats, e.g., a decrease in the malonyldialdehyde (MDA) levels when hepatocytes are exposed to an inducer of lipid peroxidation, and a recovery in the glutathione (GSH) levels upon damaging induction. Thus, the hepatoprotective properties of the herbal compositions of the present invention may in part be as a result of their antioxidant properties and the inhibition of the spread of free radicals.

The herbal compositions of the present invention also possess regenerative or proliferative properties. Thus, in one aspect of the present invention, the herbal compositions of the present invention are useful for the regeneration of liver cells in patients.

The presence of chemical groups of secondary metabolites, such as phenols, tannins, terpenoids, lactones and coumarins, in the selected plant organs of the genera and species of interest may explain, at least in part, some of the biological actions observed.

In another broad aspect, the invention is related to a method for the treatment or prevention of hepatic disorders in a patient comprising administering to a patient a therapeutically effective amount of an herbal composition of the present invention. The hepatic disorder may be caused by a viral infection, such as hepatitis B and/or C, or a non-viral hepatic disorder, such as fibrosis, cirrhosis and non-viral hepatitis.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE PREFERRED EMBODIMENTS

For the purposes of the present invention, the term "extract" means a concentrate of water-soluble and/or alcohol-soluble and/or other appropriate solvent-soluble, such as hexane-soluble and chloroform-soluble, plant components from the portion of the plant extracted and can be in liquid or solid (e.g., powder) form.

The invention will now be described in terms of following examples.

EXAMPLE 1

Hydroalcohol extract of *Cordia* spp: 250 g of *Cordia lutea* flowers were dried by dehydration and then macerated with 1-1.5 litres of a hydroalcoholic solution (ethanol-water in a ratio of about 65:35 to about 75:25) for 6 to 8 days at room temperature. The macerated flowers in ethanol were then concentrated at low pressure using a standard rotoevaporator. The residual formed was then freeze-dried and sterilized. A 14-22 g mass was obtained in the raw extract, yielding 6-9% of the sample mass. A 5 mg/ml stock solution was prepared for testing by dissolving 5 mg in 0.7% ethanol/distilled water.

EXAMPLE 2

Hydroalcohol extract of *Annona* spp: 250 g of *Annona muricata* leaves were dried using an oven at a temperature of about 45 to 55 degrees Celsius. The dried leaves were then subjected to a grinding process using a standard blade grinder. The powder obtained was sifted until particle size fraction measured between about 0.35 to about 0.10 millimetres. The powder was then macerated with 1-1.5 litres of a hydro-alcoholic solution (ethanol-water in a ratio of about 65:35 to about 75:25) for 6 to 8 days at room temperature. The macerated powder in ethanol was then concentrated at low pressure using a standard rotoevaporator. The residual was then freeze-dried and sterilised. A 14-22 g mass was obtained in the raw extract, yielding 5-8% of the sample mass. A 5 mg/ml stock solution was prepared for testing by dissolving 5 mg in 0.7% ethanol/distilled water.

EXAMPLE 3

Hydroalcohol extract of *Curcuma* spp: 250 g of *Curcuma longa* roots were dried using an oven at a temperature of 45 to 55 degrees Celsius. The dried roots were then subjected to a grinding process using a standard blade grinder. The powder obtained was sifted until particle size fraction measures between 0.35 and 0.10 millimetres. Then it is macerated with 1-1.5 litres of a hydro-alcoholic solution (ethanol-water 65:35 to 75:25) for 6 to 8 days at room temperature. This is then concentrated at low pressure using a standard rotoevaporator. The residual is then freeze-dried, sterilised. A 10-16 g mass is obtained in the raw extract, yielding 4-7% of the sample mass. A 5 mg/ml stock solution was prepared for testing by dissolving 5 mg in 0.7% ethanol/distilled water.

EXAMPLE 4

An herbal composition comprising extracts of *Cordia lutea* flowers, *Annona muricata* leaves, and *Curcuma longa* roots was prepared as follows. The freeze-dried raw extracts obtained in Examples 1, 2 and 3 were mixed in that order in the following proportions: 8 mg:1 mg:1 mg to give a weight ratio of 8:1:1 (1:0.125:0.125), respectively, and a 5 mg/ml stock solution was prepared for testing by dissolving 5 mg of the freeze-dried mixture in 0.7% ethanol/distilled water.

EXAMPLE 5

Preparation of Hepatocytes

Extracts of herbal compositions of the present invention were tested using primary rat hepatocyte cultures to determine their antioxidant effects in vitro. Typically, tests were performed using male rats (Sprague Dawley) provided by CRIFFA (Santa Perpetua de La Mogoda, Barcelona), which were held at the Fe de Valencia Hospital Research Centre until the isolation of the hepatocytes was performed. The handling and sacrifice of the animals was carried out in accordance to national regulations, the provision 609/86 of the European Union, and the principles on handling and use of laboratory animals published by the US National Institute of Health (NIH).

The isolation of the rat hepatocytes was based on the Berry and Friend method (M. N. Berry, D. S. Friend. High yield preparation of isolated rat liver parenchymal cells. *J. Cell. Biol.* 43:506-520, 1969) incorporated herein by reference, which consists of an in situ liver infusion with a solution containing collagenase, which acts as a disintegrative enzyme. Shortly after administrating anaesthesia to the animal with an intraperitoneal thiobarbital injection, an abdominal laparotomy is performed, and the vena cava is cannulated with a 1-mm diameter cannula. Initially, a saline solution is perfused to clean the organ using a peristaltic pump adjusted to a flow of 18-20 ml/min. Once this process is finalized, the collagenase solution is added to disintegrate the liver. The cellular suspension obtained during this process is filtered and centrifuged, and, after removing the collagenase, is resuspended in the culture, and the cells are cultured in an appropriate extracellular matrix.

The suspension of the cells obtained in the different isolations was cultured with a density of $8 \times 10^4$ viable cells/cm$^2$ in 96-well plates to observe the formation of free radicals and cytotoxicity. Glutathione quantification and lipid peroxidation were evaluated in cells cultured in 24-well plates. Prior to culturing the hepatocytes, the plates were covered with fibronectin (3.5 µg/cm$^2$). The cells were cultured in a Ham's F-12/Lebovitz L-15 (1:1) medium, complemented with sodium selenite (170 µg/ml), newborn calf serum at 2%, penicillin (50 mU/ml), streptomycin (50 µg/ml), serum bovine albumin at 0.2%, and insulin (10 nM). After the resuspension, an aliquot was obtained to perform a cell count and determine their viability using the trypan blue exclusion method. The degree of incorporation of the trypan blue into the cells depends on the integrity of the plasma membrane, and, thus, it can be used as an indicator of cell death. Therefore, trypan blue at 0.4% was added to a cell suspension aliquot and the cells that were not dyed blue were counted in five different fields using a microscope and a Neubauer chamber. The percent viability was calculated as follows:

$$\% \text{ Viability} = \frac{\text{Number of non-blue cells}}{\text{Total number of cells}} \times 100$$

Cell Viability Using Dimethyl-Tetrazolium (MTT)

Cellular viability was determined by measuring the uptake and reduction of dimethyl-tetrazolium (MTT), a pale yellow substrate, to formazan, a blue insoluble metabolite. This cellular reduction reaction measures mitochondrial dehydrogenase activity, which activity depends on the degree of integrity of the organelle, and thus is a clear indicator of the number of viable cells in the culture. In this case, MTT is used as a tetrazolium salts substrate which shows a yellow colour, and, with the mitochondrial dehydrogenase succinate activity, generates a blue insoluble metabolite (formazan), which can be quantified by measuring the absorption using an ELISA reader, which measures absorption in the range of 405-630 nm.

With the exception of the tests where exposure was too brief, for example, in the production of free radicals, during the remainder of the lipid peroxidation and glutathione tests, a cellular viability study was performed in parallel. Rat hepatocytes cultured in a 96-well plate were incubated in identical conditions as in the other experiments. Once the incubation period was completed, the MTT was added to the culture and was incubated for two hours. The formazan that was generated was dissolved in dimethyl sulfoxide (DMSO) and, eventually, its absorption was evaluated at 550 nm by an ELISA reader. The cells that were not treated with herbal compositions were used as a positive viability control (M. J. Gomex-Lechon and J. V. Castell. In Vitro Toxicity Testing. In: Cell and Tissue Culture Laboratory Procedures. Ed. J. B. Griffiths, A. Doyle and D. G. Newell. ISBN: 0471928526. John Wiley & Sons Ltd. Baffins Lane, England, 1998; 12B: 5.6; J. V. Castell, M. J. Gomez-Lechon, In vitro alternatives to animal pharmaco-toxicology. Farmaindustria Ed. J V Castell and M J Gomez-Lechon. Madrid, 1992; M. J. Gomez-Lechon, T. Donato, X. Ponsoda, R. Fabra, R. Trullenque and J. V. Castell. Isolation, culture and use of human hepatocytes in drug research. IN VITRO METHODS IN PHARMACEUTICAL RESEARCH. ISBN 0-12-163390-X. Eds.; J. V. Castell and M. J. Gomez-Lechon eds. pp. 129-154. Academic Press. London (1997), incorporated herein by reference).

Production of Free Radicals

In order to quantify the production of free radicals, primary cultures of rat hepatocytes, cultured in a 96-well plate, were incubated with herbal compositions of the present invention at the following concentrations: 4, 20, 100 and 500 µg/ml, along with 5-chloromethyl-2',7'-dichlorohydrofluorescein (DCFH-DA), a fluorescent agent which spreads well through the plasma membrane due to his apolar property and its non-ionic structure, and, when oxygen is present, emits fluorescence (Lautraite S, Bigot-Lasserre D, Bars R and Carmichael N. Optimisation of cell-based assays for medium throughput screening of oxidative stress. *Toxicol in vitro* 17:207-220 (2003), incorporated herein by reference). Once the incubation period is completed, the cells were exposed to t-butylhydroperoxide (t-BOOH), with the herbal composition present, and immediately thereafter, the fluorescence emission was read ($t_0$) at 485 nm (stimulation) and 527 nm (emission). Eventually, the cells were incubated at 37° C. and fluorescence was read in 30-minute intervals for a period of 2 h. Cells treated with quercetin (a flavonoid with known antioxidant activity) were used as a positive control of the test (Boots A. W., Bast A. and Haenen G. R. No role of DT-diaphorase (NqO1) in the protection against oxidized quercetin. *FEBS Lett* 579: 677-682, incorporated herein by reference). Quantification was expressed in % of free radicals with respect to control (cells induced with oxidative stimulation, in the absence of herbal composition). In order to quantify the free radicals, herbal compositions were first dissolved in ethanol-water solution in a range of 0.5-1%.

Lipid Peroxidation and Glutathione Reduction

To measure lipid peroxidation and glutathione reduction, the isolated rat liver cells were cultured in 24-well plates with at a density of 80,000 viable cells/cm$^2$. After a stabilisation period of the 1-hour culture, the cells were pre-incubated with herbal composition at 4, 20, 100 and 500 µg/ml during a 24-hour period. Once the pre-incubation was finalised, the cells were exposed to t-BOOH 250 µM with the active ingredient of the formulas subject of this invention, using the concentrations stated above. Once the 24 h period elapsed, the cells were collected and centrifuged at 1200 rpm for 5 minutes; then the liquid was recovered to measure the production of malonyldialdehyde (MDA). The mono-layers were washed and frozen to evaluate the protein and glutathione levels (GSH). The non-treated cells were used as controls of the basal oxidation, and the cells treated exclusively with t-butylhydroperoxide were used as controls of the induced oxidation.

Lipid peroxidation was determined by quantifying the production of MDA in the culture (M. J. Gomex-Lechon and J. V. Castell. In Vitro Toxicity Testing. In: Cell and Tissue Culture Laboratory Procedures. Ed. J. B. Griffiths, A. Doyle and D. G. Newell. ISBN: 0471928526. John Wiley & Sons Ltd. Baffins Lane, England, 1998; 12B: 5.6; J. V. Castell and M. J. Gomez-Lechon, In vitro alternatives to animal pharmaco-toxicology. Farmaindustria Ed. J. V. Castell and M. J. Gomez-Lechon. Madrid, 1992; M. J. Gomez-Lechon, T. Donato, X. Ponsoda, R. Fabra, R. Trullenque and J. V. Castell. Isolation, culture and use of human hepatocytes in drug research. IN VITRO METHODS IN PHARMACEUTICAL RESEARCH. ISBN 0-12-163390-X. Eds. J. V. Castell and M. J. Gomez-Lechon eds. pp. 129-154. Academic Press. London (1997), all incorporated herein by reference). In order to perform this quantification, the cells were incubated and then centrifuged at 1,200 rpm for 5 minutes to eliminate the cellular debris. The liquid recovered was incubated at 100° C. for 60 minutes in the dark, with a buffer containing SDS at 7%, HCl 0, 1N, phosphotungstic acid at 1%, and thiobarbiturate acid at 0.67%. The samples were subjected to extraction, added 1 ml of butanol, and were centrifuged at 3,000 rpm for 10 minutes. The reading of the organic phase (supernatant) at 530 nm (stimulation) and 595 (emission) determined the MDA formation in the incubation conditions of the herbal composition tested. The MDA diluted in the culture was used as the standard. The non-treated cells were used as negative controls of the basal oxidation, and the cells treated exclusively with t-BOOH were used as positive controls of the induced oxidation. Protein concentration in the cell monolayers was used to normalize the data.

Glutathione (GSH) level quantification was performed through a fluorometric reaction with o-phthalaldehyde (OPT) (M. J. Gomex-Lechon and J. V. Castell. In Vitro Toxicity Testing. In: Cell and Tissue Culture: Laboratory Procedures. Ed. J. B. Griffiths, A. Doyle and D. G. Newell. ISBN: 0471928526. John Wiley & Sons Ltd. Baffins Lane, England, 1998; 12B: 5.6; J. V. Castell, M. J. Gomez-Lechon, In vitro alternatives to animal pharmaco-toxicology. Farmaindustria Ed. J V Castell and M J Gomez-Lechon. Madrid, 1992; M. J. Gomez-Lechon, T. Donato, X. Ponsoda, R. Fabra, R. Trullenque and J. V. Castell. Isolation, culture and use of human hepatocytes in drug research. IN VITRO METHODS IN PHARMACEUTICAL RESEARCH. ISBN 0-12-163390-X. Eds. J. V. Castell and M. J. Gomez-Lechon eds. pp. 129-154. Academic Press. London (1997), all incorporated herein by reference). The cells incubated for 24 hours with the concentrations of herbal composition aforementioned were sonicated in a buffer (trichloroacetic acid at 5% and EDTA mM) for 1-2 seconds. Sodium phosphate (0.1 M), NaOH (1M) and an OPT dissolution was added to the liquid aliquot obtained after centrifuging the plate at 3,000 rpm for 30 minutes. The samples sonicated for 1-2 s were kept in the darkness for 30 minutes to read the fluorescence at 360 (stimulation) 450 nm (emission). GSH 10 mM diluted in a homogenisation buffer was used as the standard. The basal glutathione level was obtained from non-treated cells, and t-BOOTH was used as a positive control on the GSH level decrease. Protein evaluation in the cells monolayers was used to normalize the data.

EXAMPLE 6

Increasing concentrations of the herbal composition of Examples 1, 2, 3 and 4 were tested for the production of free radicals, lipid peroxidation and glutathione levels, as described above, using isolated rat hepatocytes. The results obtained are shown in Table 1 below.

TABLE 1

Hepatoprotective effect in vitro of the herbal composition of Examples 1, 2, 3 and 4 on the samples where t-BOOH oxidant agent was applied - Values are shown as a mean ± standard error of the mean. *p < 0.05 as a percentage of the group treated with t-BOOH.

| Treatments | Concentration (µg/mL) | Free radicals (%)* | Lipid peroxidation (pmols MDA/mg protein) | Glutathione level (nmols GSH/mg protein) |
|---|---|---|---|---|
| Untreated cells | | 00 | 00 | 65.0 ± 13.0 |
| t-BOOH | 500 µM | 100 ± 14.2 | 822.2 ± 41.1 | 9.2 ± 0.7 |
| Example 1 | 4 | 79.5 ± 1.4 | 754.0 ± 5.5 | 10.4 ± 3.1 |
| Example 2 | 4 | 103.8 ± 6.2 | 1,055.5 ± 54.8 | 33.3 ± 2.3 |
| Example 3 | 4 | 93.8 ± 4.9 | 725.5 ± 135.7 | 27.2 ± 1.3 |
| Example 4 | 4 | 77.6 ± 1.4 | 1,054.6 ± 88.4 | 36.3 ± 5.1 |
| Example 1 | 20 | 43.8 ± 1.6 | 671.3 ± 88.8 | 17.9 ± 5.4 |
| Example 2 | 20 | 56.6 ± 10.7 | 956.5 ± 200.2 | 29.8 ± 1.6 |
| Example 3 | 20 | 48.2 ± 2.9 | 650.3 ± 0.0 | 27.1 ± 0.7 |
| Example 4 | 20 | 41.4 ± 8.9 | 530.3 ± 0.0 | 29.5 ± 5.2 |
| Example 1 | 100 | 16.2 ± 0.3 | 112.0 ± 0.0 | 53.3 ± 0.3 |

TABLE 1-continued

Hepatoprotective effect in vitro of the herbal composition of Examples
1, 2, 3 and 4 on the samples where t-BOOH oxidant agent was applied - Values
are shown as a mean ± standard error of the mean. *p < 0.05 as a percentage of the
group treated with t-BOOH.

| Treatments | Concentration (μg/mL) | Free radicals (%)* | Lipid peroxidation (pmols MDA/mg protein) | Glutathione level (nmols GSH/mg protein) |
|---|---|---|---|---|
| Example 2 | 100 | 17.8 ± 2.8 | 431.8 ± 104.0 | 51.1 ± 3.6 |
| Example 3 | 100 | 20.3 ± 1.1 | 410.4 ± 72.5 | 45.2 ± 1.5 |
| Example 4 | 100 | 15.9 ± 0.4 | 153.8 ± 10.2 | 54.8 ± 5.9 |
| Example 1 | 500 | 4.1 ± 0.5 | 70.9 ± 17.8 | — |
| Example 2 | 500 | 00 | 0.0 ± 0.0 | — |
| Example 3 | 500 | 6.1 ± 0.5 | 383 ± 33.7 | — |
| Example 4 | 500 | 3.7 ± 0.3 | 0.0 ± 0.0 | — |
| Quercetin | 5 μM | 51.5 ± 2.1 | — | — |
| Quercetin | 25 μM | 18.8 ± 1.2 | — | — |

*expressed as a ratio of the positive control (t-BOOH)

As can be seen in Table 1, Example 4, the 8:1:1 weight ratio of the three extracts, i.e., Example 1 (*Cordia lutea*), Example 2 (*Annona muricata*) and Example 3 (*Curcuma longa*), consistently showed a greater effect than the individual Examples at equivalent doses, in particular, at the higher concentrations of 100 μg/mL and 500 μg/mL. This suggests a synergistic effect when all three extracts are combined in the above ratios. Of the three individual extracts tested, Example 1 showed superior results over Examples 2 and 3, suggesting that Example 1, alone or in combination, may be important for hepatoprotection of the liver.

EXAMPLE 7

Increasing concentrations of the herbal composition of Example 4 were tested for the production of free radicals and lipid peroxidation, as described above, using two independent isolated rat hepatocytes. The combined results obtained are shown in Table 2 below.

TABLE 2

Hepatoprotective effect in vitro of the herbal composition of Example 4
on the samples where t-BOOH oxidant agent was applied - Values are shown as a
median ± standard error of the median. *p < 0.05 with respect to the group treated
with t-BOOH.

| Treatments | Concentration (μg/mL) | Free radicals (%)* | Lipid peroxidation (pmols MDA/mg protein) | Glutathione level (nmols GSH/mg protein) |
|---|---|---|---|---|
| Non-treated cells | | 0 | 0 | 38.5 ± 9.2 |
| t-BOOH | 1 | 100 | 2147.3 ± 539.0 | 7.5 ± 0.4 |
| Example 4 | 4 | 71.2 ± 8.7* | 2337.2 ± 522.6 | 14.5 ± 4.9 |
| | 20 | 34 ± 10.3* | 915.4 ± 175.0 | 11.5 ± 4.1 |
| | 100 | 12.0 ± 5.4* | 83.0 ± 34.0 | 39.9 ± 9.6* |
| | 500 | 2.2 ± 2.2* | 27.0 ± 18.6 | 37.6 ± 10.8* |
| Quercetin | 25 μM | 13.2 ± 5.6* | — | — |

*expressed as a ratio of the positive control (t-BOOH)

As can be seen in Table 2, the incubation of the herbal composition of Example 4 with t-BOOH reduces the formation of free radicals. This protective action of the herbal composition of Example 4 was dose dependent and is comparable to the reduction of free radicals that took place in the cells incubated with quercetin, a known antioxidant. While the 100 and 500 μg/ml concentrations showed an almost total blocking action on oxidation of the t-BOOH, a substantial decrease to about 34% was observed even at the lower concentration of 20 μg/ml.

The results from the lipid peroxidation evaluation through MDA quantification using the herbal composition of Example 4 showed a similar behaviour, since the MDA levels decrease as the herbal composition of Example 4 concentration increases, as shown in Table 2.

Table 2 also shows the effects of pre-incubation of the hepatocytes with the herbal composition of Example 4 on GSH using two independent rat hepatocyte cultures. These values are compared to the reduction induced by the t-BOOH oxidant. The GSH levels increased as the concentration of herbal composition of Example 4 increased; the GSH levels were essentially the same as with non-treated cells at the 100 and 500 μg/ml concentrations, showing that at high concentrations Example 4 essentially restores normal GSH protein levels.

A parallel cell viability study was performed on the lipid peroxidation and glutathione tests. When the pre-incubation period and the herbal composition of Example 4 treatment were completed, no toxicity was seen in the isolated rat hepatocytes, i.e., essentially 100% viability was observed even at the highest concentrations indicating that the composition of Example 4 was essentially non-toxic to isolated rat hepatocytes at the highest levels.

From the above results, it can be seen that the herbal composition of Example 4 acts as an antioxidant that blocks the formation of free radicals, and thus, reduces lipid peroxidation. In addition, the GSH levels are preserved, in particular, when concentrations of 100 μg/mL or higher of Example 4 are used. Thus, the herbal composition of Example 4 may also act as a hepatoprotective composition for the liver.

The herbal composition of Example 4 also showed greater clinical improvements (see below) and was more efficacious at reducing various symptoms caused by liver damage as a result of hepatitis C infection. In particular, less nausea and less burning sensation in the stomach was observed with patients taking the mixture of all three herbal extracts, as opposed to taking individual extracts separately. This further suggests that there may be additional benefits in taking a mixture of all three extracts as is the case with Example 4.

EXAMPLE 8

The genotoxic effect of the composition of Example 4 on human lymphocytes from peripheral blood was assessed using the Alkaline Electrophoresis Test on Individual Cells (The Comet Test), which is performed on a primary culture of human lymphocytes in order to evaluate the potential for genetic damage caused by the active ingredient of this invention (M. J. Gomez-Lechon, T. Donato, X. Ponsoda, R. Fabra, R. Trullenque and J. V. Castell. Isolation, culture and use of human hepatocytes in drug research. IN VITRO METHODS IN PHARMACEUTICAL RESEARCH. ISBN 0-12-163390-X. Eds. J. V. Castell and M. J. Gomez-Lechon eds. pp. 129-154. Academic Press. London (1997), incorporated herein by reference).

The cell culture used lymphocytes obtained from 20 mL of total blood from a healthy donor; the lymphocytes were isolated through differential centrifugation and the use of 20 mL of Lymphoprep (Sigma). After centrifugation, the cell ring of lymphocytes was extracted with a pipette. The cells were later washed with PBS and were centrifuged at 1,000 rpm for 10 min. Finally, the cell button was resuspended in 6 mL of freezing medium until it was used in the different experiments performed. Lymphocytes were exposed for 1 hour at 37° C. to the following concentrations of the composition of Example 4: 100, 200 and 500 μg/mL.

One hundred cells were analysed in each treatment and the moment of change of state as an indicator of the damage. The Comet 5 analysis program was used for this analysis, which is a genotoxicity test that detects primary damage to the DNA in the cells (Genet. Mol. Res. 2(4): 410-417 (2003), incorporated herein by reference). The statistical analysis on the results obtained was performed using the non-parametric test Kruskal Wallis, $p<0.05$.

The active ingredients of Example 4 did not induce any damage to the DNA (which would be detected as ruptures in a simple chain and spots that are labile to alkali) when applied up to 500 μg/mL in peripheral blood lymphocytes, under these test conditions.

EXAMPLE 9

The acute toxicity of Example 4 extract was tested using the Limit Dose Test in albino mice (Balb/C/CNPB) and the Acute Toxic Class Test in albino rats (Holtzmann) as follows.
Limit Dose Test
The extract of Example 4 and a control substance (a saline solution) were administered orally using an intragastric catheter according to the following:
Species: Albino Mice (*Mus musculus*)
Inbred: Balb/C/CNPB
Number of animals: 10 animals per experimental group
Sex: Male and female
Body weight: 20-25 g.
Group I (Under Treatment): These animals were administered a dose of 2,000 mg/kg of the extract of Example 4.
Group II (Control): These animals were administered a solvent or saline solution (same as extract volume).

The mice underwent a fasting period of 4 hours prior to the experiment; then, the product was administered accordingly and the animals were under continuous observation for 4 hours. Upon no occurrence of mortality, the observation period was extended to 14 days after the extract was administered, and then up to 21 days, in order to perform an observation of the recovery of the animals and the reversibility of the effects.

The body weight of the animals was recorded at the beginning of the experiment, as well as on the 7th, 14th and 21st day when possible after the substances were administered, in order to establish whether there was a weight loss or gain.

At the end of the experiment, the animals were sacrificed through a cervical dislocation procedure, where the skull is separated from the spine by applying pressure to the base of the skull and the cervical column. This way, there is no sensitivity to pain, since the spinal cord is separated from the encephalon.

A necropsy was performed on all the animals that survived until the end of the experiment. In the case of the animals that died during the experiment, the colour, size, and weight of their organs were evaluated.

The macroscopic analysis of the organs did not find any visible changes in the Group I mice where the extract (Example 4) was administered at a dose of 2,000 mg/kg. The results obtained show the innocuousness of the extract at a dose of 2,000 mg/Kg. p.c., since no mortality and no clinical signs or macroscopic changes were observed, and thus there was no evidence of toxicity in the organs.

In summary, the Limit Dose Method showed that the freeze-dried aqueous extract Example 4 did not cause any deaths at a dose of 2,000 mg/kg administered orally. Thus, the freeze-dried aqueous extract Example 4 may be classified as NON-TOXIC $ATC_0$, meaning that it is not classifiable through the Limit Dose Method.
Acute Toxic Class (ATC) Test
The extract of Example 4 and a control substance (a saline solution) were administered orally using an intragastric catheter according to the following:
Species: Albino rats (*Rattus novergicus*)
Inbred: Holtzmann
Number of animals: 3 animals per experimental group
Sex: Male and female
Body weight: 120-160 g.
Group I (Under Treatment): These animals were administered a dose of 2,000 mg/kg of the extract of Example 4.
Group II (Control): These animals were administered a solvent or saline solution (same as extract volume).

This experiment was performed using male and female rats, which underwent a week-long quarantine, were divided in two groups composed of three animals of each sex, and were weighed and marked for identification purposes. Before the evaluation, the animals underwent a fasting period of 12 hours; then, the extract of Example 4 and the control substance were administered to both groups according to the dose table. Immediately after the substances were administered, the animals were observed to look for toxic signs at system/organ level: Autonomous, behaviour, sensory, neuromuscular, respiratory, ocular, gastrointestinal, urinary, and others, such as body weight. The body weight of the animals was recorded on the 7th and 14th day after the substances were administered.

After 14 days, the animals were sacrificed following the ethical principles for animal experimentation; this was followed by a macroscopic study to analyse the size, colour and consistency of the following organs: heart, kidneys, liver, spleen, stomach, lung, brain, ovaries and testicles. The macroscopic analysis of the organs did not find any visible changes where the extract was administered at a dose of 2,000 mg/kg.

The results obtained show the innocuousness of the extract at a dose of 2,000 mg/kg Example 4, since no mortality and no clinical signs or macroscopic changes were observed, thus finding no evidence of toxicity in the organs. Hence, according to the Acute Toxic Class Method, the freeze-dried aqueous extract Example 4 did not cause any deaths at a dose of 2,000 mg/kg administered orally. Thus, the freeze-dried aqueous extract Example 4 may be classified as NON-TOXIC $ATC_0$, meaning that it is not classifiable through the Acute Toxic Class Method.

EXAMPLE 10

An uncontrolled clinical study was performed on 10 adult Caucasian patients (5 male and 5 female, aged between 37 and 58), all of them diagnosed with chronic hepatitis C, and three of them with hepatitis B in addition to C. All of them showed the symptoms of chronic hepatitis and some had previously received antiviral therapy without getting good results. The estimated time, from the history, of the virus infection varied between 4 and 30 years.

The duration of symptomatic disease, according to the clinical history, ranged from 1 to 12 years. The evaluation of the state of each patient was performed through their clinical history (including symptoms and signs), as well as serologic, biochemical, and ultrasound studies performed at the beginning of the treatment and after 28 days of treatment with the composition used in Example 4

The presence of hepatitis C was identified through the detection of anti-HCV, using a second-generation Elisa System. The presence of hepatitis B was confirmed through an analysis of surface antigen (HBs Ag) and core antigen (HBc Ag.). The hepatological damage was assessed through HCV FIBROSURE (550123). A study was conducted using three-dimensional ultrasound to determine the liver's volume, the characteristics of its borders and the ultrasound alterations of the liver parenchyma. The assessment of characteristics of the portal vein, the spleen and the presence of ascites were also included in the study.

The biochemical study of the alterations produced by chronic hepatitis B and C were based on four criteria: (1) tests to measure the synthesis capacity of the liver; (2) tests to measure alterations caused by fibrosis leading to intrahepatic obstruction (evaluation of bilirubin and phosphatase levels); (3) tests to measure necro-inflammatory activity in the hepatocytes, including a test to assess hepatocarcinoma (measurement of the glutamate pyruvate transaminase (GPT), glutamate oxalate transaminase (GOT), gamma-glutamyl transpeptidase (GGT) and alpha-fetoprotein (AFT)); and (4) tests to measure the liver's detoxification function (measurement of ammonia).

Prior to treatment, symptoms, such as general discomfort, fatigue and joint aches and pains, were observed in all (100%) of the 10 patients; depression was observed in 90%, muscular pain was felt by 80% of the patients, and lack of concentration and sleep disorders were found in 60% and 50% patients respectively. Headache was observed in 30% of the patients. Gastro-intestinal symptoms, such as indigestion (abdominal discomfort and/or gastric acidity) was observed in 60% of the cases; nausea was found in 50% of the patients, and intestinal dysfunction reached 40%; while dyspepsia, sensation of fullness, and abdominal pain were reported in 30% of the cases. The clinical exam showed that the most frequent finding was abdominal pain to palpation, especially on the right hypochondrium and the epigastrum, which was observed in 70% of the cases; jaundice and palpable liver were found in 20% of the patients, while ascites, palpable spleen, ecchymoses, and lower limb edema appeared in 10%.

To determine the level of success of the treatment with Example 4 on quality of life (in terms of health) of the 10 patients with chronic hepatitis C, the psychological, biological and clinical effects of the treatment were also recorded. The Health Quality of Life Questionnaire (HQLQ) is a validated instrument that measures the quality of life based on a group of generic indicators of the SF-36 report, which consists of a set of eight parameters. These parameters measure physical endurance (RP), body pain (BP), perception of general health (GH), vitality (VT), social functioning (SF), limitations due to emotional factors (RE), and mental health (MH), and are aggregated and used as parameters to develop the Physical Component Summary (PCS) and the Mental Component Summary (MCS).

The evaluation before the treatment showed that all of the patients had difficulty walking more than a mile, compared to 21.9% of the general population, 50% of patients had difficulty climbing stairs, compared to 7.1% of the general population, 55.5% of the patients showed limitations in walking 100 yards, compared to 14.1% of the general population; 100% of the patients said they had difficulties in performing their work, compared to only 45% of the general population; 30% of the patients studied stated that pain interfered with their ability to work, compared to 9.5% of the general population; and 90% of the patients reported a "regular" or "poor" state of health, compared to 13.1% of the general population. Overall, the quality of life related to the health of the 10 patients with chronic hepatitis C, was substantially compromised.

All ten patients were treated with 140 mg of the composition of Example 4, three doses per day, for 28 days. The patients' diet was varied; however, excessive fat consumption was avoided and there was no alcohol consumption. After 28 days of treatment with the composition of Example 4, the following changes were observed.

There were significant changes in the ultrasound readings in 90% of the patients. In six cases, there was a reduction in diffuse echogenicity compared to reading taken before the treatment and a reduction in the size of the liver and the spleen. In three cases, the echography showed stable signs when compared to the first control reading, and in one case, the patient evolved unfavorably, showing an increase in the echogenicity and ascites.

Clinical evaluation following treatment with the composition of Example 4 showed a reduction in the general symptoms from 60% to 80% on average, general discomfort was reduced in 70%, osteo-articular pain, severe fatigue was reduced by 60%, depression and osteo-muscular pain decreased in 60% and 50% respectively, lack of concentration and sleep disorders decreased to 40% and 20%. The patients who still suffered from these general symptoms experienced a decrease in their intensity. This study also showed a reduction in gastrointestinal symptoms. Indigestion and intestinal dysfunction decreased by 30%; dyspepsia decreased to 20% and nausea to 10%, while abdominal pain was not present in any case. Patients that continued to suffer from gastrointestinal discomfort reported that the intensity had decreased. When the treatment with the composition of Example 4 was completed, the pain to the touch on the right hypochondrium was reduced to 20%. Other signs such as jaundice, palpable liver, ascites, lower-limb edema, ecchymosis and palpable liver, remained unchanged at 20% and 10% respectively.

The study on the quality of life related to health was based on information gathered through the Health Quality of Life Questionnaire (HQLQ), which uses a set of generic parameters from the SF-36 health report. This report uses a set of norms obtained from data gathered from the general population in the United States. These norms average 50 points with a Standard Deviation of 10; high scores indicate a better state of health. The quality of life study showed that, prior to treatment, the quality of life of the 10 patients was substantially compromised. However, the evaluation performed after the treatment with the composition of Example 4 for 28 days, showed that the HQL of 6 patients was restored to normal or higher-than-normal levels (above 50); three patients showed HQL restored close to normal levels (several points in the SF-36 scale were close to or higher than 50, while some others were slightly below 50). Only one case retained a low health quality of life score.

Biochemical tests of hepatic function performed before the treatment (initial control record) and 28 days after the treatment with the composition of Example 4 showed that, following treatment, three patients experienced a substantial increase in cholinesterase levels (between 71.1% and 81.1%); in two cases there was a moderate increase (between 62.1% and 54.9%); in four cases there was an increase of between 34% and 40%; and one case showed a minimal increase of 15.7%. Therefore, 90% of the patients had normal capacity to synthesize this enzyme, suggesting a functional recovery of the hepatocytes. Prothrombin concentrations increased following treatment (between 24.8% and 33.3%) in four cases with a moderate increase (between 8.8% and 19.2%) in another four cases; an insignificant decrease of 0.5% in one patient, and a decrease of 9.0% in the other case. Overall, 70% of the patients reached normal levels, and showed evidence of functional recovery in their hepatocytes.

A comparison between the pre-albumin readings at the time of the initial control (before the treatment) and that of the final control (28 days after the treatment with the composition of Example 4), showed a significant increase of between 19.5% and 26.9% in three patients, insignificant variations of 0.0% and 5.0% in other three patients, while the other four cases experienced a reduction between 18.0% and 28.2%. Therefore, seven of the ten patients reached normal levels, whereas at the beginning of the treatment, there were only four patients with normal readings indicating a recovery in the hepatocyte function.

Tests were also performed to measure intrahepatic obstruction (cholestasis); a comparison between bilirubin readings at the time of the initial control and that of the final control of the treatment with the composition of Example 4, showed a decrease of 36.9%, 15.4% and 4.6% in three patients, respectively, who initially had higher-than normal levels bilirubin. One patient, who initially had higher-than normal levels, reported an increase of 23.3%. The other six cases did not have higher-than normal levels initially and did not show any change with treatment. A comparison between alkaline phosphatase readings at the time of the initial control and that of the final control of the treatment with the composition of Example 4, showed an increase of 23.9% in the one patient that had higher-than normal levels prior to treatment. The other nine patients stayed within normal levels.

With regards to the indices of inflammation and hepatic injury, a comparison between the GPT readings at the time of the initial control and that of the final control of the treatment with the composition of Example 4 showed a decrease of between 6.2% and 84.7% in six patients who initially had higher-than normal levels of this element. The other two patients who initially had higher-than normal levels, reported an increase of 16.1% and 57.5% and the other two cases remained at normal levels. A comparison between the GOT levels at the time of the initial control and that of the final control of the treatment with the composition of Example 4, showed a decrease of between 3.8% and 74.3% in five patients who initially had higher-than normal levels. The other three cases had normal levels before and after treatment.

A comparison between the GGT readings at the time of the initial control and that of the final control of the treatment with the composition of Example 4, showed a decrease of between 11.3% and 48.6% in three patients who initially had higher-than-normal levels of this element; two other patients reported an increase of 2.1% and 5.7% respectively, and the other five cases stayed within normal levels. AFT readings at the time of the initial control and that of the final control of the treatment with the composition of Example 4, showed that nine patients started the treatment with normal values; eight were still normal at the end of the treatment and one experienced a slight increase (8.5%); the remaining patient, who started the treatment with high levels of this substance, maintained high levels.

In order to evaluate the detoxication capacity of the hepatocyte, the ammonia levels were also recorded. Ammonia readings at the time of the initial control and that of the final control of the treatment with the composition of Example 4 showed that nine patients started and finished with normal levels, while the other one with higher-than normal levels at the beginning of the study finished with an above the normal level.

Transferrin readings at the time of the initial control and that of the final control of the treatment with the composition of Example 4 showed that one patient, who initially had higher-than normal levels, finished the treatment at normal levels; two patients, who initially had higher-than normal levels, continued above those normal levels, and the patients that started with normal levels stayed within normal limits.

In summary, the evaluation performed after the 28-day treatment with the composition of Example 4 established that there was a significant reduction in the symptoms observed in the patients, a moderate improvement in the hepatic illness indicators and a significant improvement in the enzymes measuring the hepatocyte damage. In the group of patients with evidence of hepatic injury there was a reduction in the indices of damage as well as by echosonography. No patient showed an increase in his/her symptoms, hematological alterations or other complications. The evolution of the patients who had evidence of active hepatitis improved more than those with advanced fibrosis (cirrhosis).

The results obtained from the clinical trial demonstrate that the herbal compositions of the present invention improve hepatic function, as well as improve the regenerative and proliferative properties of hepatocytes. These compositions may be used prophylactically, since they prevent or minimize the adverse effects caused by viral infections, or the action of other agents that induce hepatic dysfunction.

Therefore, the herbal compositions of the present invention are useful in the treatment of hepatic disorders caused by viral infection, autoimmune reactions, ingestion of drugs, xenobiotics or toxins.

EXAMPLE 11

The composition of Example 4 was tested on a 46 year old female patient who suffered from chronic hepatitis B and C, in non-fibrotic state, with a virus inoculation period of 4 years and 1 year of illness, who did not consume anti-viral medications. The composition of Example 4 was administered orally, three 140 mg doses per day for 28 days. The patient's clinical symptoms were controlled, echographic exams and biochemical analyses were performed on her before and 28 days after the treatment.

Treatment with the composition of Example 4 during 28 days succeeded in eliminating general symptoms shown by the patient before starting the treatment (general discomfort, severe fatigue, sleep disorders, depression, joint and muscular pain). In addition, with the treatment, gastrointestinal symptoms like indigestion and pain upon palpation disappeared.

The echographic control performed on the $28^{th}$ day showed that there was a favourable evolution in the reduction of the diffuse echogenicity that the patient showed before the treatment.

The biochemical analyses are shown in Table 3.

TABLE 3

Biochemical study performed in a patient with chronic hepatitis B and C who received a treatment with the composition of Example 4 for 28 days

| Variables (normal values) | Before treatment | $28^{th}$ day of treatment |
|---|---|---|
| Pre-albumin (<20 mg/dl) | 27.0 | 19.4 |
| Prothrombin Time (11 sec) | 13.0 | 11.8 |
| Prothrombin Concentration (100%) | 80.0 | 96.6 |
| GPT (0.0-38.0 UI) | 71 | 51 |
| GOT (0.0-40.0 UI) | 55 | 41 |
| GGT (9.0-35.0 U/L) | 72 | 37 |

The treatment with the composition of Example 4 did not affect the normal levels of total bilirubin, direct bilirubin, indirect bilirubin, AFP, ammonia, TNF alpha and platelet count.

The results in this example show that the composition of Example 4 can reduce liver damage induced by hepatitis B and C co-infection.

EXAMPLE 12

The composition of Example 4 was tested on a 47 year old female patient who suffered from chronic hepatitis C, in non-fibrotic state, with a virus inoculation period of 15 years and 5 years of illness, who did not consume anti-viral medications. The composition of Example 4 was administered orally, three 140 mg doses per day, for 28 days. The patient's clinical symptoms were controlled, echographic exams and biochemical analyses were performed on her before and 28 days after the treatment.

Treatment with the composition of Example 4 for 28 days succeeded in eliminating general symptoms shown by the patient before starting the treatment (general discomfort, sleep disorders, joint pain). In addition, the treatment with the composition of Example 4 diminished or eliminated general symptoms like muscular pain and headache, as well as gastrointestinal symptoms like nausea, intestinal dysfunction and pain upon palpation.

The echographic examination performed on the $28^{th}$ day showed a reduction of the diffuse echogenicity that the patient showed before the treatment.

The biochemical analyses are shown in Table 4.

TABLE 4

Biochemical study performed in a patient with chronic hepatitis B and C who received a treatment with the composition of Example 4 for 28 days

| Variables (normal values) | Before treatment | $28^{th}$ day of treatment |
|---|---|---|
| Pre-albumin (<20 mg/dl) | 25.0 | 18.1 |
| Prothrombin Time (11 sec) | 13.0 | 11.5 |
| Prothrombin Concentration (100%) | 80.0 | 100 |
| GPT (0.0-38.0 UI) | 50 | 32 |
| GOT (0.0-40.0 UI) | 41 | 31 |
| Transferrin (300-360 ug/dl) | 377 | 339 |

Treatment with the composition of Example 4 did not affect levels of total bilirubin, direct bilirubin, indirect bilirubin, Alkaline Phosphatase, GGT, AFP, ammonia, TNF alpha and the platelet count, which were normal prior to treatment.

Results from this example show that the composition of Example 4 can reduce liver damage induced by the hepatitis C infection.

EXAMPLE 13

The phytochemical profiles of the hexane and hydroalcoholic extracts of the genera of the present invention were obtained as follows. A 125 g sample of each of the selected organs of each of the relevant species was taken. Hexane (an apolar solvent) was used to perform an exhaustive extraction at room temperature, renewing the solvent every 48 hours. The hexane extract was obtained upon eliminating the solvent in a low-pressure rotoevaporation process. The residual from the hexane extraction was then treated with ethanol-water (70:30) and an exhaustive extraction was carried out. Afterwards, the ethanol-water solvent was removed until the product was completely dry.

The phytochemical profile was obtained in accordance with the methodology described by Chhabra, S. C. et al. Phytochemical Screening of Tanzanian Medical Plants. J. Ethnopharmacol. (1984) 11(2): 157-79, incorporated herein by reference, in order to determine the chemical groups of secondary metabolites present in the species. Only the alkaloids required extraction in basic medium. The phytochemical profiles of the flowers of *Cordia* spp, the leaves of *Annona* spp and the roots of *Curcuma* spp are shown in Tables 5, 6 and 7, respectively.

TABLE 5

Phytochemical profile of flower samples from the *Cordia* species
Mass of the vegetal sample: 125 grams

| | Hexane Extract | Hydroalcoholic Extracts (EtOH/Water: 70/30) |
|---|---|---|
| Mass Obtained: 11.25 g | 1.93 g | 9.32 g |
| % of Mass Obtained | 17.16% | 82.84% |
| 1 Alkaloids | − | + |
| 2 Saponins | ND | ++ |
| 3 Steroids | − | − |
| 4 Triterpenoids | ++ | ++ |
| 5 Tannins | ND | +++ |

TABLE 5-continued

Phytochemical profile of flower samples from the *Cordia* species
Mass of the vegetal sample: 125 grams

|   |   | Hexane Extract | Hydroalcoholic Extracts (EtOH/Water: 70/30) |
|---|---|---|---|
| 6 | Phenols | ND | +++ |
| 7 | Flavonoids | ND | ++ |
| 8 | Quinones | − | + |
| 9 | Lactones and Coumarins | ++ | +++ |
| 10 | Lipids and essential oils | − | ND |
| 11 | Amines and amino acids | ND | ++ |

TABLE 6

Phytochemical profile of leaf samples from the *Annona* species
Mass of the vegetal sample: 125 grams

|   |   | Hexane Extract | Hydroalcoholic Extracts (EtOH/Water: 70/30) |
|---|---|---|---|
|   | Mass Obtained: 14.87 g | 5.77 g | 9.10 g |
|   | % of Mass Obtained | 38.80% | 61.20% |
| 1 | Alkaloids | − | + |
| 2 | Saponins | ND | + |
| 3 | Steroids | ++ | ++ |
| 4 | Triterpenoids | − | − |
| 5 | Tannins | ND | +++ |
| 6 | Phenols | ND | +++ |
| 7 | Flavonoids | ND | + |
| 8 | Quinones | − | ++ |
| 9 | Lactones and Coumarins | + | +++ |
| 10 | Lipids and essential oils | − | ND |
| 11 | Amines and amino acids | ND | ++ |

TABLE 7

Phytochemical profile of root samples from the *Curcuma* species
Mass of the vegetal sample: 125 grams

|   |   | Hexane Extract | Hydroalcoholic Extracts (EtOH/Water: 70/30) |
|---|---|---|---|
|   | Mass Obtained: 11.58 g | 3.95 g | 7.63 g |
|   | % of Mass Obtained | 34.11% | 65.89% |
| 1 | Alkaloids | − | − |
| 2 | Saponins | ND | − |
| 3 | Steroids | − | − |
| 4 | Triterpenoids | +++ | +++ |
| 5 | Tannins | ND | +++ |
| 6 | Phenols | ND | +++ |
| 7 | Flavonoids | ND | ++ |
| 8 | Quinones | + | +++ |
| 9 | Lactones and Coumarins | +++ | +++ |
| 10 | Lipids and essential oils | +++ | ND |
| 11 | Amines and amino acids | ND | ++ |

LEGEND:
(−) Negative Test
(+) Positive Test;
ND: This test was not done on this extract;
CONTENT:
(+) Little
(++) Medium
(+++) Much The results obtained from the flowers of the *Cordia* species in Table 5 shows the strong presence of phenols, tannins, lactones and coumarins in the hydroalcoholic extract from a flower sample from this species.

EXAMPLE 13

A tablet form of the composition of Example 4 used in the above patient studies was formulated to give 300-mg coated tablets with 140 mg of the composition of Example 4.
The tablet composition is shown in Table 8.

TABLE 8

Coated Tablet Pharmaceutical Formula

| Component | Contents % |
|---|---|
| Composition of Example 4 | 46.6 |
| Cellulose | 21.5 |
| Cornstarch | 20.9 |
| Polyvinylpyrrolidone | 4.3 |
| Talcum | 3.4 |
| Aerosil 200 | 0.5 |
| Magnesium Stearate | 0.5 |
| Hydroxypropylmethyl Cellulose | 2.0 |
| Tween 80 | 0.3 |

The composition of the present example can also be formulated as capsules (300 mg) as shown in Table 9.

TABLE 9

Gel Capsule Pharmaceutical Formula

| Component | Contents % |
|---|---|
| Composition of Example 4 | 46.6 |
| Cornstarch | 9.4 |
| Polyvinylpyrrolidone | 44 |

Finally, a suspension of the compositions of the present invention can also be formulated as follows. A flavoured suspension was produced with 1% of the herbal compositions of the present invention to provide 140 mg of the herbal composition per 15 ml dose (one spoon). The suspension's composition is shown in Table 10.

TABLE 10

Flavoured Suspension Pharmaceutical Formula

| Component | Contents % |
|---|---|
| Composition of Example 4 | 1 |
| Sorbitol | 19.61 |
| Sodium Benzoate | 0.21 |
| Sodium Metabisulfite | 0.13 |
| Glycerine | 3.27 |
| Sodium Saccharin | 0.06 |
| Raspberry Flavour | 0.01 |
| Edetate Disodium, Dihydrate | <0.01 |
| Ethanol | 1 |
| Deionised Water c.s.p. | 74.7 |

The formulas were produced in accordance to the Good Manufacturing Practices (BPL) Guidelines.

Preferably, the three formulas described above are administered three times per day, 30-60 minutes before meals.

Pharmaceutical formulas can include herbal compositions of the present invention in their liquid, solid and semi-solid forms, so that the active ingredients therein can be discharged quickly or slowly. The administration of the pharmaceutical formulas of this invention can be oral, rectal, intravenous, intramuscular, hypodermic, topical or through other methods, in one dose, multiple doses, through slow or quick discharge methods or a deposit. The invention may be embodied in various other forms which are understood by those in the art.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

What is claimed:

1. An herbal composition for treating hepatic disorders, formulated as an oral tablet or capsule, comprising a hepatoprotective amount of *Cordia lutea*, wherein *Cordia lutea* is the flowers or extracts thereof, and one or more selected from the group consisting of *Annona muricata* or *Curcuma longa*, or both, wherein *Annona muricata* is the leaves or extracts thereof; wherein *Curcuma longa* is the roots or extracts thereof.

2. The herbal composition of claim 1, comprising both *Annona muricata* leaves and *Curcuma longa* roots, or an extract thereof.

3. The herbal composition of claim 1, wherein the *Cordia lutea* comprises *Cordia lutea* flowers or an extract of *Cordia lutea* flower and either *Annona muricata* leaves or *Curcuma longa* roots, or both.

4. The herbal composition of claim 3, wherein the hepatoprotective amount of *Cordia lutea* flowers and either *Annona muricata* leaves or *Curcuma longa* roots, or both, comprises an extract of *Annona muricata* leaves or *Curcuma longa* roots or both.

5. The herbal composition of claim 2, wherein the hepatoprotective amount of *Cordia lutea* flowers, *Annona muricata* leaves and *Curcuma longa* roots comprises extracts of *Cordia lutea* flowers, *Annona muricata* leaves and *Curcuma longa* roots.

6. The herbal composition of claim 5, wherein the extracts of *Cordia lutea* flowers, *Annona muricata* leaves and *Curcuma longa* roots are present in a weight ratio of about 1:1:1 to about 8:1:1, respectively.

7. The herbal composition of claim 5, wherein the extracts of *Cordia lutea* flowers, *Annona muricata* leaves and *Curcuma longa* roots are present in a weight ratio of about 1:0.025-1:0.025-1, respectively.

8. The herbal composition of claim 5, wherein the extracts of *Cordia lutea* flowers, *Annona muricata* leaves and *Curcuma longa* roots are present in a weight ratio of about 8:1:1, respectively.

9. The herbal composition of claim 8, wherein the extracts are hydroalcoholic extracts.

10. An herbal composition for treating hepatic disorders, formulated as an oral tablet or capsule, comprising a hepatoprotective amount of *Cordia lutea*, wherein *Cordia lutea* is the flowers or extracts thereof, said composition having hepatoprotective properties.

11. The herbal composition of claim 10, wherein the extract is a hydroalcoholic extract.

* * * * *